United States Patent [19]

Sinha

[11] Patent Number: 5,739,432
[45] Date of Patent: Apr. 14, 1998

[54] ULTRASONIC CHARACTERIZATION OF SINGLE DROPS OF LIQUIDS

[75] Inventor: Dipen N. Sinha, Los Alamos, N. Mex.

[73] Assignee: The Regents of the University of California, Los Alamos, N. Mex.

[21] Appl. No.: 657,709

[22] Filed: May 30, 1996

[51] Int. Cl.[6] ................................................. G01N 29/00
[52] U.S. Cl. .................... 73/579; 73/61.49; 73/61.75; 73/61.79; 73/64.53
[58] Field of Search ........................... 73/579, 597, 599, 73/64.53, 54.41, 61.45, 61.49, 61.75, 64.42, 580, 657

[56] References Cited

U.S. PATENT DOCUMENTS

| | | | |
|---|---|---|---|
| 3,392,574 | 7/1968 | Lemon et al. | 73/64.53 |
| 4,179,936 | 12/1979 | Bennett et al. | 73/606 |
| 4,478,072 | 10/1984 | Brown et al. | 73/61.75 |
| 4,558,589 | 12/1985 | Hemmes | 73/64.42 |

FOREIGN PATENT DOCUMENTS

| | | | |
|---|---|---|---|
| 4313216 | 10/1994 | Germany | 73/579 |
| 744281 | 6/1980 | U.S.S.R. | 73/64.53 |
| 1188643 | 10/1985 | U.S.S.R. | 73/64.53 |

OTHER PUBLICATIONS

D. J. McClements and P. Fairley. "Frequency Scanning Ultrasonic Pulse Echo Reflectometer." Ultrasonics 30, 403 (1992).

F. Eggers and Th. Funck. "Ultrasonic Measurements with Milliliter Liquid Samples in the 0.5–100 MHz Range." Rev. Sci. Instrum. 44, 969 Aug., 1973.

A. P. Sarvazyan. "Development of Methods of Precise Ultrasonic Measurements in Small Volumes of Liquids." Ultrasonics 20, 151 Jul. 1982.

*Primary Examiner*—Hezron E. Williams
*Assistant Examiner*—Nashmiya Ashraf
*Attorney, Agent, or Firm*—Samuel M. Freund

[57] ABSTRACT

Ultrasonic characterization of single drops of liquids. The present invention includes the use of two closely spaced transducers, or one transducer and a closely spaced reflector plate, to form an interferometer suitable for ultrasonic characterization of droplet-size and smaller samples without the need for a container. The droplet is held between the interferometer elements, whose distance apart may be adjusted, by surface tension. The surfaces of the interferometer elements may be readily cleansed by a stream of solvent followed by purified air when it is desired to change samples. A single drop of liquid is sufficient for high-quality measurement. Examples of samples which may be investigated using the apparatus and method of the present invention include biological specimens (tear drops; blood and other body fluid samples; samples from tumors, tissues, and organs; secretions from tissues and organs; snake and bee venom, etc.) for diagnostic evaluation, samples in forensic investigations, and detection of drugs in small quantities.

15 Claims, 5 Drawing Sheets

ULTRASONIC CHARACTERIZATION OF SINGLE DROPS OF LIQUIDS

The invention was made with government support under Contract No. W-7405-ENG-36 awarded by the U.S. Department of Energy to The Regents of the University of California. The government has certain rights in this invention.

FIELD OF THE INVENTION

The present invention relates generally to the characterization of liquids and, more particularly, to the characterization of small quantities of liquids, typically a drop or less, using ultrasonic interferometry.

BACKGROUND OF THE INVENTION

In many situations, such as in the study of snake venom or other precious chemical or biological specimens, the amount of liquid available for characterization is very small. In diagnosing biological samples, for example tear drops, contaminated tissue samples, tumors samples, etc., sample sizes are at most a single drop of liquid. Currently, there are no simple procedures for the measurement of sound speed and sound attenuation for samples of this size. Frequency-dependent sound speed and attenuation measurements over a wide frequency range are important for determining particle size distributions in emulsions and for determination of various chemical and molecular relaxation times. Moreover, such information is necessary for identification of constituent chemicals and characterization of liquids and mixtures.

As stated, ultrasonic characterization of liquids involves the determination of sound speed and sound attenuation over a range of frequencies. Instruments which perform this function are readily available commercially. The most common approach is the pulse technique where the propagation of a short (microsecond or less) ultrasonic pulse through the liquid is measured. In such measurements, the pulse propagation time (time-of-flight) provides the sound speed measurement if the pulse propagation distance through liquid is known. Sound attenuation is derived from the amplitude of the pulse after propagating through the liquid. Since pulses have large frequency content, it is possible to derive frequency-dependent measurements of sound speed and attenuation by Fourier transformation of the propagated signal. A frequency scanning ultrasonic pulse echo reflectometer (FSUPER) recently developed by D. J. McClements and P. Fairly, is described in "Frequency Scanning Ultrasonic Pulse Echo Reflectometer," Ultrasonics 30, 403 (1992).

The FSUPER system requires a fast digital oscilloscope or data digitizer and Fourier transformation (FFT) of the data. The electronics for performing such operations is expensive and bulky. A sufficient volume of liquid is required so that the propagation length is at least 1 cm. Using water for the liquid, the pulse propagation time would be approximately 6 ms (assuming 1500 m/s for the sound speed in water). To obtain a sound speed resolution of 0.5 m/s, a digital oscilloscope of at least 500 MHz bandwidth (corresponding to 2 ns time resolution) is required. For high quality measurements, signal averaging of a large number of pulses is required.

For a single drop of a liquid, the dimensions involved are small and the relevant distance is approximately 1 mm. The time of flight becomes subnanosecond which would require GHz sampling rate data-acquisition systems. Moreover, the transducers for such measurements must be broadband, and expensive high-frequency electronics are required.

An alternative to pulse-echo measurements for sound speed and attenuation is the ultrasonic interferometer technique invented several decades ago. In this technique, one sets up standing waves in the liquid medium between two piezoelectric crystals (transducers). Typically, one transducer is used for generation of the standing waves, while a second transducer, positioned opposite to and parallel to the first transducer, detects the standing waves. The liquid is placed between these two transducers. Standing waves are generated at certain frequencies which are the function of sound speed in the liquid and the distance between the transducers. If the excitation frequency is swept over a chosen frequency range, a number of approximately equally spaced interference peaks are detected by the second transducer. These interference peaks result from resonances (standing waves) in the liquid path. The spacing between any two consecutive interference peaks ($\Delta f$) is directly related to the speed of sound, c, in the liquid by the relationship: $c_n = 2d\Delta f_n$, where d is the separation between the two transducers, and n is the order of the interference peak. The sound attenuation, $\alpha_n$, is obtained from the width of a resonance curve, $\delta f_n$, from the relationship $\alpha_n = \pi \delta f_n / c$. For a single drop of liquid, $2d$ is approximately 1.5 mm, which produces interference peaks at about 1 MHz intervals. Such measurements are readily achieved with inexpensive electronics equipment.

Since interferometry techniques require only the generation of standing waves in a small liquid-filled cavity, power requirements are several orders of magnitude less than that required for typical pulse-echo measurements. That is, in contrast to the typical >100 V required for transducer excitation for the latter measurements, excitation voltages for interferometry measurements are <1 V. Moreover, a single frequency sweep provides all of the needed frequency-dependent measurements. Most importantly, instrumentation requirements are modest. Instead of gigahertz sampling oscilloscopes, only common rf (radio frequency) MHz-type frequency generation and measurement equipment are required. Although various researchers (See, e.g., F. Eggers and Th. Funck, "Ultrasonic Measurements with Milliliter Liquid Samples in the 0.5–100 MHz Range," Rev. Sci. Instrum. 44, 969 (1973), and A. P. Sarvazyan, "Development of Methods of Precise Ultrasonic Measurements in Small Volumes of Liquids," Ultrasonics 20, 151 (1982)) have shown that such measurements are achievable using small amounts (~1 ml) of liquids, it has not been shown that interferometry can be adapted to measurements on single drops (microliters) of liquid. Nor have measurements been made in the absence of containers.

Accordingly, it is an object of the present invention to provide a containerless apparatus for ultrasonic characterization of liquid-droplet-size samples.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the containerless apparatus for ultrasonically characterizing a single droplet of a liquid includes: a first transducer having an open or unblocked surface; a second transducer having an open or unblocked surface, the open surface of the second transducer being spaced-apart a chosen distance from, and disposed opposite to the open surface of the first transducer such that the droplet is held therebetween by surface tension; means for applying ultrasonic excitation having a chosen frequency to the first transducer, whereby standing waves are generated in the droplet which cause an electrical signal to be produced in the second transducer; and means for detecting the electrical signal.

Preferably, the apparatus further includes means for sweeping the ultrasonic excitation from the means for applying ultrasonic excitation to the first transducer over a chosen range of ultrasonic frequencies.

Preferably the apparatus also includes means for measuring the frequency of the standing wave generated in the droplet, whereby a resonance spectrum of the liquid droplet is obtained.

It is also preferred that means are provided for changing the distance between the open surface of the first transducer and the open surface of the second transducer to accommodate various droplet sizes or materials.

In a second embodiment of the present invention, in accordance with its objects and purposes, and as broadly described herein, the containerless apparatus for ultrasonically characterizing a single droplet of a liquid hereof includes: a transducer having an open or unblocked surface; a reflector having a substantially planar surface, the planar surface of the reflector being spaced-apart a chosen distance from, and disposed opposite to, the open surface of the transducer such that the droplet is held therebetween by surface tension; means for applying ultrasonic excitation having a chosen frequency to the transducer, whereby standing waves are generated in the droplet; and means for measuring the electrical impedance of the transducer.

Preferably, the apparatus further includes means for sweeping the ultrasonic excitation from the means for applying ultrasonic excitation to the transducer over a chosen range of ultrasonic frequencies.

Preferably also the apparatus includes means for measuring the frequency of the standing wave generated in the droplet, whereby a resonance spectrum of the liquid droplet is obtained.

It is also preferred that the apparatus include means for changing the distance between the planar surface of the transducer and the planar surface of the reflector.

It is preferred that the reflector is transparent so that the droplet may be optically observed.

In yet another embodiment of the present invention, in accordance with its objects and purposes, and as broadly described herein, the method for ultrasonically characterizing a single droplet of a liquid hereof includes the steps of: applying ultrasonic excitation having a chosen frequency to the droplet using a pair of closely, spaced transducers between which the droplet is suspended by surface tension, whereby standing waves are generated therein; and detecting the generated standing waves.

Preferably, the method further includes the step of sweeping the applied frequency of ultrasonic excitation over a chosen range of frequencies, whereby a resonance spectrum of the liquid droplet is obtained.

Benefits and advantages of the present invention include a requirement only for droplet-size or smaller samples, and apparatus cleansing between samples is facilitated by the containerless feature thereof and the small surface area in contact with the sample.

BRIEF DESCRIPTION OF THE DRAWINGS

The accompanying drawings, which are incorporated in and form a part of the specification, illustrate two embodiments of the present invention and, together with the description, serve to explain the principles of the invention. In the drawings:

FIG. 5 shows data obtained from the apparatus shown in FIG. 4, hereof, for a layer of water between a transducer and a glass plate.

DETAILED DESCRIPTION

Briefly, the present invention includes the use of two closely-spaced transducers, or one transducer and a closely spaced reflector plate, to form an interferometer suitable for ultrasonic characterization of droplet-size and smaller samples without the need for a container. The droplet is held between the interferometer elements, whose distance apart may be adjusted, by surface tension. The surfaces of the interferometer elements may be readily cleansed by a stream of solvent followed by purified air when it is desired to change samples. A single drop of liquid is sufficient for high-quality measurement. Examples of samples which may be investigated using the apparatus and method of the present invention include biological specimens (tear drops; blood and other body fluid samples; samples from tumors, tissues, and organs; secretions from tissues and organs; snake and bee venom, etc.) for diagnostic evaluation, samples in forensic investigations, and detection of drugs in small quantities.

Figure 1:
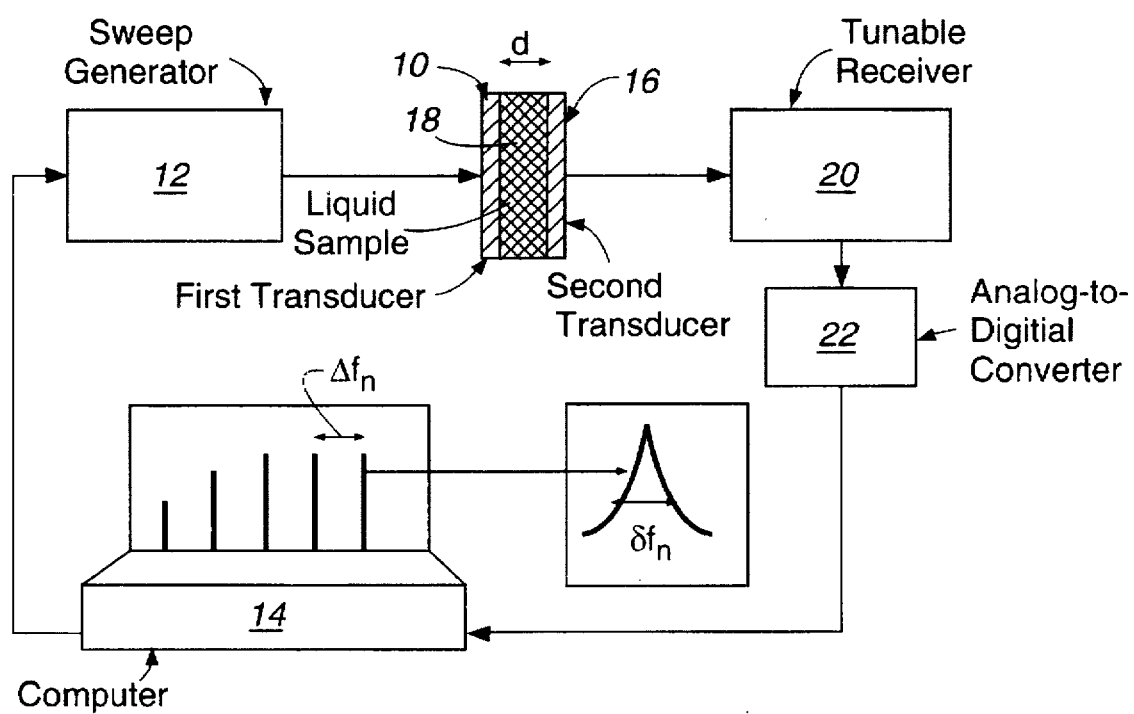
FIG. 1 is a schematic representation of one embodiment of the apparatus of the present invention, showing the use of two transducers for forming an interferometer.

Reference will now be made to the present preferred embodiments of the invention, which are illustrated in the accompanying drawings. Identical or similar structure is identified by identical callouts. Turning now to FIG. 1, a schematic illustration of one embodiment of the apparatus of the present invention is illustrated. A first transducer, 10, is energized by sweep generator, 12, controlled by computer, 14. A commercially available Digital Synthesizer and Analyzer PC plug-in board was used. This system allows the frequency to be swept up to a frequency of 10 MHz with 0.1 Hz frequency resolution over the entire range. A second transducer, 16, is spaced-apart from and disposed opposite to first transducer, 10. A liquid sample, 18, is held between the transducers by surface tension. Acoustical excitation from the first transducer is transmitted through the liquid and impinges upon the second (receiver) transducer which generates an electrical signal in response thereto. The output signal from the receiver transducer is detected and amplified (gain=100) by tunable receiver, 20, and analyzed using either heterodyne (amplitude measurement only) or homodyne (both amplitude and phase measurement) detection. No signal averaging of multiple sweeps was found to be required, since the resulting apparatus is equivalent to a narrow-band (~100 Hz) tracking filter that provides excellent immunity from extraneous noise and offers a signal-to-noise ratio of 98 dB. A single-sweep measurement is sufficient. The analog output from receiver 20 is converted by an analog-to-digital converter, 22, to a digital signal which is processed by computer 14.

The distance between the two transducers may be adjusted. As the ultrasonic excitation frequency is swept through a chosen range of frequencies, standing waves are produced in the liquid sample. As stated hereinabove, the frequencies at which this occurs (resonance frequencies) are related to the properties of the liquid (speed of sound therein) and the spacing between the transducers. The frequency width of the resonances is a function of the sound attenuation by the liquid sample. It should be mentioned that the open, oppositely disposed surfaces of the transducers do not have to be planar and parallel. Curved surfaces, where the radius of curvature is larger than the separation between the surfaces, assists the measurement by focusing the ultrasonic beam. This has the added advantage of reducing diffraction at lower frequencies.

Figure 2:
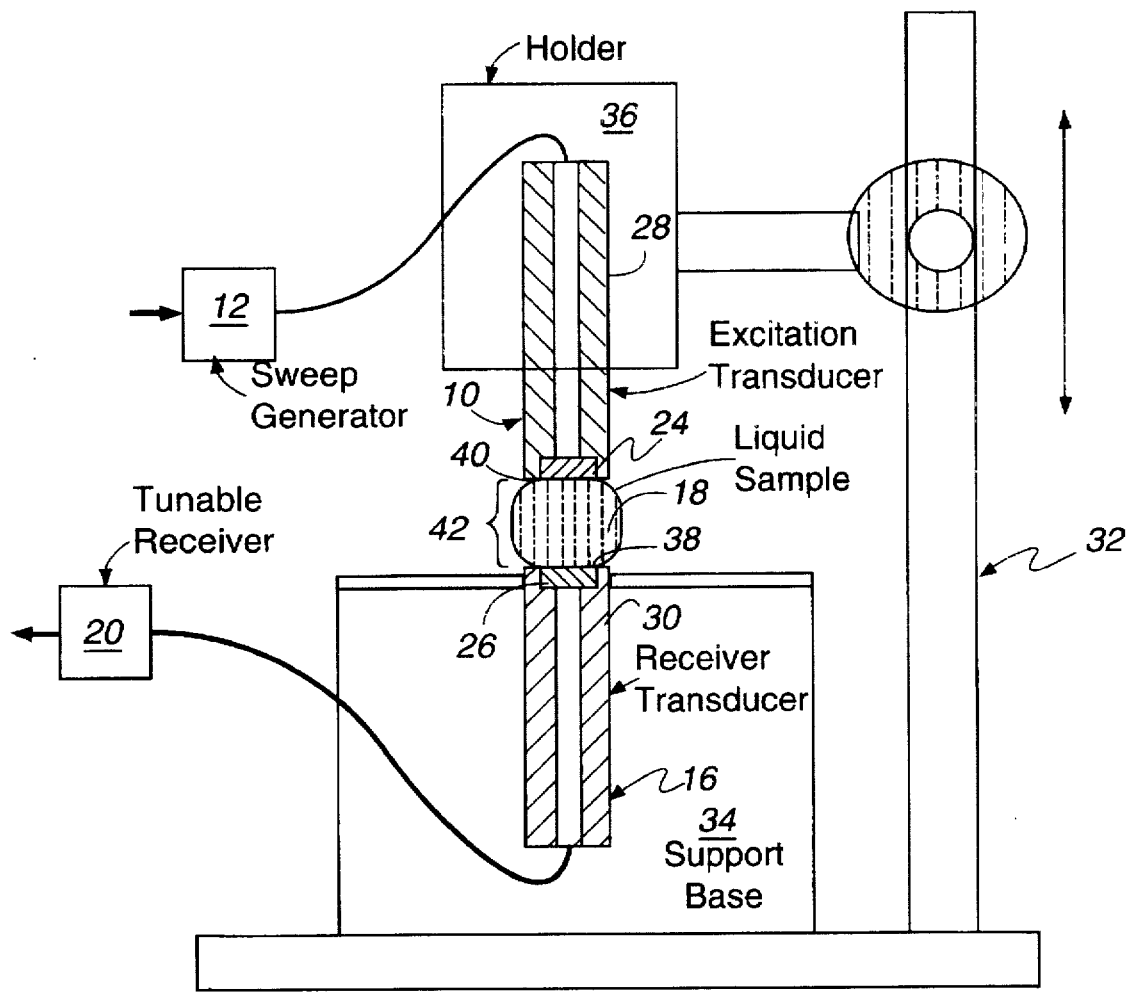
FIG. 2 is a schematic representation of an expanded view of the transducers utilized for measurement on droplet-size samples and smaller samples.

FIG. 2 is a schematic representation of an expanded view of the transducers utilized for measurement on droplet-size samples and smaller samples. Commercially available transducers 10, 16, consisting of 0.53 mm diameter quartz crystals, 24 and 26, respectively (5 MHz center frequency), each encased in a shielded metal tube, 28 and 30, respectively, were positioned parallel to and a chosen distance from each other using micrometer, 32. The transducers can be positioned vertically (one above the other) or horizontally with identical results. One of the transducers (shown as excitation transducer 10) is movable while the position of the other (receiver transducer 16) is fixed in support base, 34. A holder, 36, permits the parallel positioning of the crystal faces. Liquid sample 18 is placed on the face, 38, of fixed transducer 16 and the liquid clings to this surface because of surface tension. Movable transducer 10 is then gently lowered such that it touches drop 18, and such that its surface, 40, is parallel to surface 38 of transducer 16. As soon as the second transducer touches the liquid sample, surface tension of the liquid forces the liquid sample to form a continuous bridge between the two transducer faces. The micrometer is adjusted such that the separation, 42, between the two faces is of the order of 1 mm. This separation can be reduced if required and increased if a larger sample volume is available. Crystals having center frequencies greater than 5 MHz are available, if required.

Figure 3:
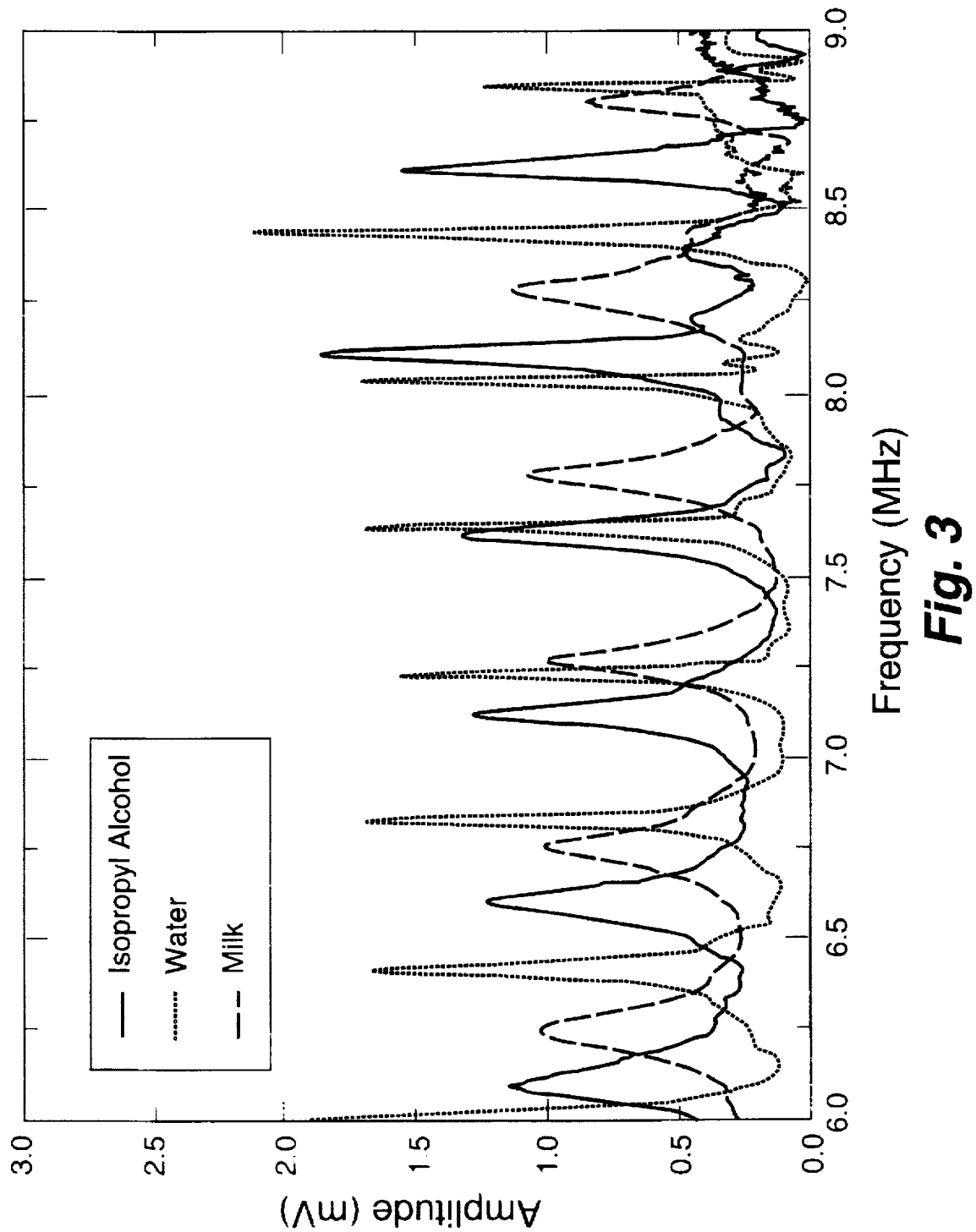
FIG. 3 shows typical data (signal amplitude versus applied excitation frequency) obtained using the present apparatus for droplet-size samples of isopropyl alcohol, water and milk.

FIG. 3 shows the ultrasonic characterization, using the instrument described hereinabove, of droplets of isopropyl alcohol, water and milk as liquid samples. The liquid volume used for these measurements was approximately 5 µl. The variations in amplitude of the peaks are due to the characteristics of the broadband transducers used. Amplitudes are not important for this type of measurements, however. Because of the 10 MHz upper limit of the electronics, measurements were limited to that frequency range. Other electronics systems such as a 15 MHz Network Analyzer can provide higher frequency range measurements, if necessary. For many types of liquid characterizations, however, a frequency range up to 10 MHz is sufficient.

A feedback loop can be used to lock onto a single interference peak and any change in sound speed can then be monitored as a function of time by following the frequency using a frequency counter. A differential-type measurement system may be constructed where reference sample measurements are compared with a particular sample to detect the presence of small variations. This can be accomplished by having two, side-by-side transducer systems within an enclosure so that there are no temperature variations between the two.

Figure 4:
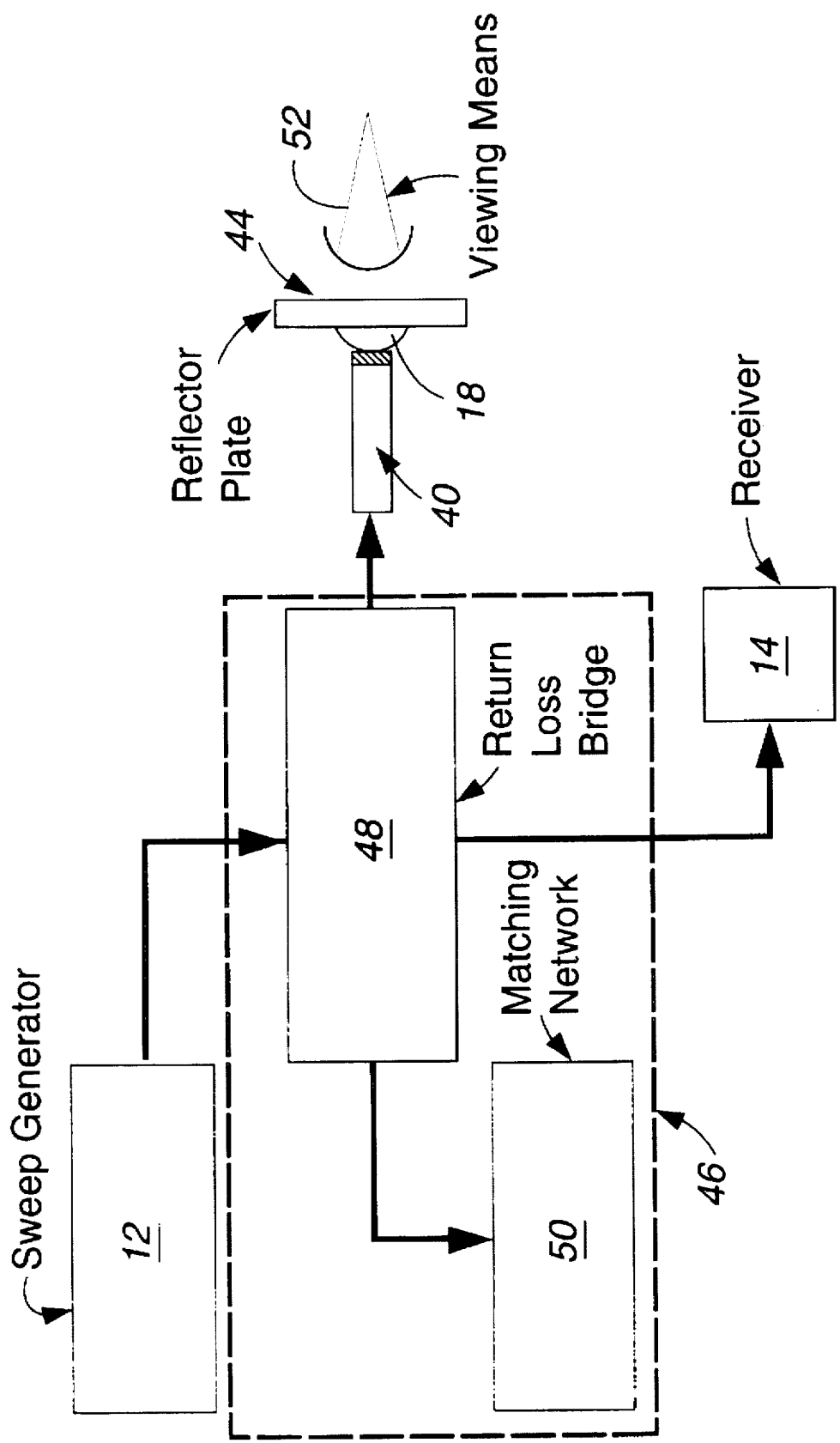
FIG. 4 is a schematic representation of another embodiment of the apparatus of the present invention showing the use of a reflector as one wall of the interferometer and a transducer as the other, and electrical impedance measurement and driving electronics for the sole transducer.
Figure 3:
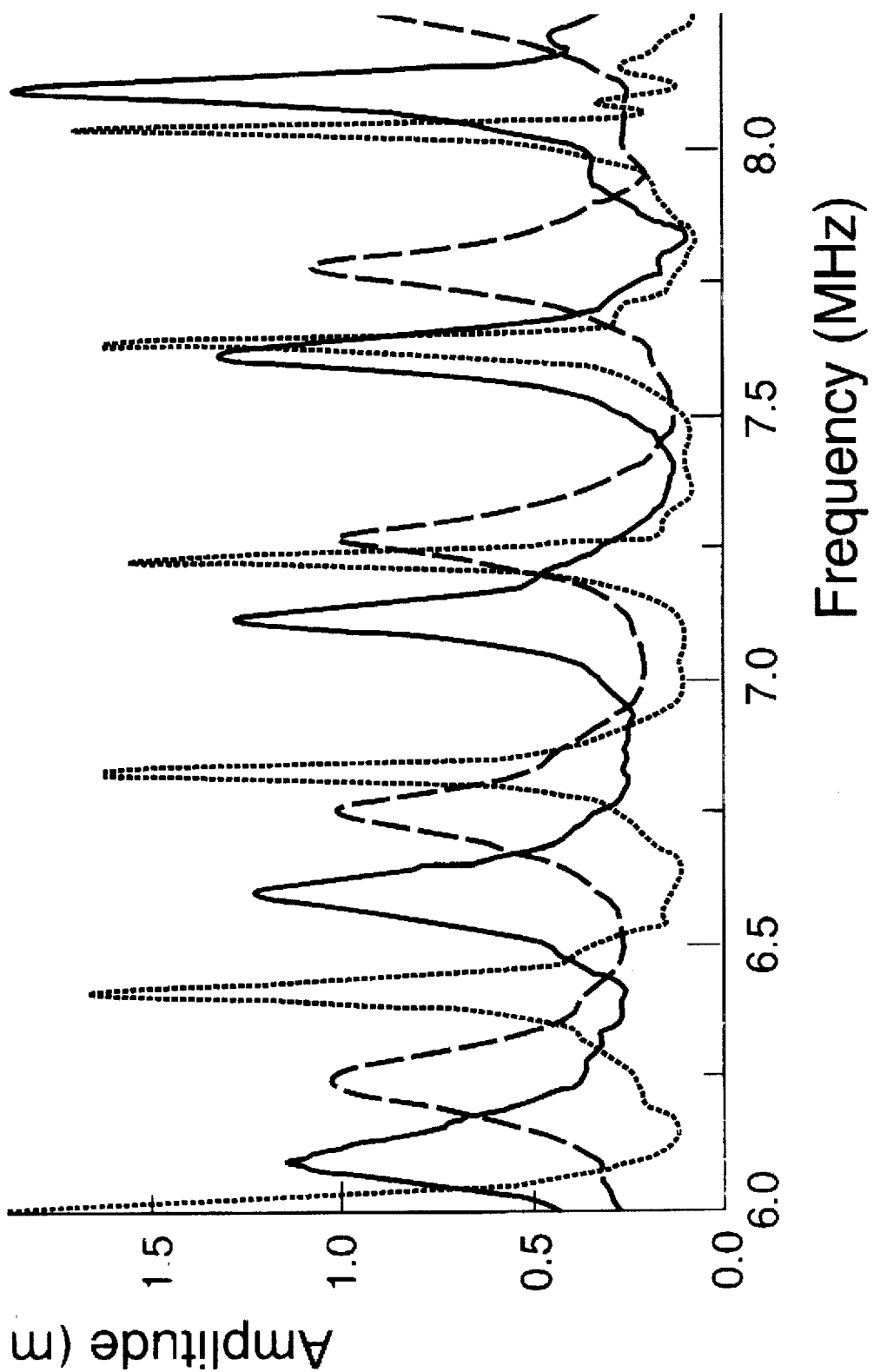

FIG. 4 is a schematic representation of another embodiment of the invention, where only a single transducer 10 is required for both ultrasonic excitation of the sample and receiving the response thereto, and a planar reflector plate, 44, is used to form the second wall of the interferometer. Interferometer face spacing and relative location would be adjusted in the same manner as described in FIG. 2 hereof, for the two-transducer apparatus. For the reasons stated hereinabove, it is not necessary that the open face of the sole transducer be planar. Transducer electrical impedance measurements are performed using apparatus, 46, which includes a return loss bridge, 48, and a matching network, 50 (combination of a parallel capacitor and resistor), which is used to balance the bridge. Sweep sine-wave generator 12 is used to drive the system. Whenever a standing wave is generated, the electrical impedance of transducer 10 changes and the bridge becomes unbalanced, producing thereby an electrical signal which may be measured by receiver 14, and monitored and analyzed by the same computerized data-acquisition used for the two-transducer measurements. The impedance changes at frequencies where standing waves are generated in the liquid (between the transducer front-face and the reflector plate shown in the Figure) since the energy dissipated into the system reaches a minimum there, and the transducer need not be driven as hard. In some situations it may be desirable to optically view the sample under investigation such as clotting of blood or sample containing suspension or bacteria. Reflector plate 44 would then be fabricated from light transparent material, and the sample observed using viewing means, 52.

Because of the 0.1 Hz frequency resolution of the measurement electronics, an overall resolution of 1 part in 10 million (0.1 Hz in 1 MHz) is possible with the apparatus of the present invention. Higher frequency resolution electronics are commercially available. Such resolution is difficult to obtain using pulse techniques that use Fourier transforms to obtain frequency spectra. Moreover, if the interference peaks are curve fitted, the peak positions can be interpolated with higher resolution than the instrument capability of 0.1 Hz. Extremely small changes in sound speed can thus be measured. Measurements can be performed in less than 1 minute for most systems. This can allow almost real-time characterization of important biological specimens.

Ultrasonic interferometers that are in common use today use a cylindrical container with two disk-shaped transducers on opposite sides of the cylinder. The liquid is commonly introduced through a hole on the cylinder side. The system is enclosed and frequent mechanical adjustments are necessary to maintain parallelism between the transducers, etc. Changing liquid samples and cleaning such apparatus is also a time-consuming process. In the present apparatus, the liquid sample is free standing and requires no container. The movable transducer is easily retracted and the crystal faces readily cleaned. The actual area to be cleaned is small.

FIG. 5 shows data obtained from the apparatus shown in FIG. 4, hereof, for a layer of water between the transducer and the glass reflector plate.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for ultrasonically characterizing a single droplet of a liquid, which comprises in combination:

a. a first transducer having an open surface;

b. a second transducer having an open surface, the open surface of said second transducer being spaced-apart a chosen distance from, and disposed opposite to the open surface of said first transducer such that the droplet is held therebetween by surface tension only;

c. means for applying ultrasonic excitation having a chosen frequency to said first transducer, whereby standing waves are generated in the droplet which cause an electrical signal to be produced in said second transducer; and d. means for detecting the electrical signal, from which electrical signal, the droplet is characterized.

2. The apparatus for ultrasonically characterizing a single droplet of a liquid as described in claim 1, wherein the open surface of said first transducer, and the open surface of said second transducer are substantially planar and disposed in a parallel manner.

3. The apparatus for ultrasonically characterizing a single droplet of a liquid as described in claim 1, wherein the open surface of said first transducer and the open surface of said second transducer are curved such that the radius of curvature thereof is larger than the chosen distance between the open surface of said first transducer and the open surface of said second transducer.

4. The apparatus for ultrasonically characterizing a single droplet of a liquid as described in claim 1, further comprising means for sweeping the ultrasonic excitation from said means for applying ultrasonic excitation to said first transducer over a chosen range of ultrasonic frequencies.

5. The apparatus for ultrasonically characterizing a single droplet of a liquid as described in claim 4, further comprising means for measuring the frequency of the standing waves generated in the droplet, whereby a resonance spectrum of the liquid droplet is obtained which is characteristic of the droplet.

6. The apparatus for ultrasonically characterizing a single droplet of a liquid as described in claim 1, further comprising means for changing the distance between the open surface of said first transducer and the open surface of said second transducer.

7. A apparatus for ultrasonically characterizing a single droplet of a liquid, which comprises in combination:

a. a transducer having an open surface;

b. a reflector having a substantially planar surface, the planar surface of said reflector being spaced-apart a chosen distance from, and disposed opposite to the surface of said transducer such that the droplet is held therebetween by surface tension only;

c. means for applying ultrasonic excitation having a chosen frequency to said transducer, whereby standing waves are generated in the droplet; and d. means for measuring the electrical impedance of said transducer, from which electrical impedance, the droplet is characterized.

8. The apparatus for ultrasonically characterizing a single droplet of a liquid as described in claim 7, wherein said open surface of said transducer is substantially planar, and the open surface of said transducer and the planar surface of said reflector are disposed in a parallel manner.

9. The apparatus for ultrasonically characterizing a single droplet of a liquid as described in claim 7, wherein the open surface of said transducer is curved such that the radius of curvature thereof is larger than the chosen distance between the open surface of said transducer and the planar surface of said reflector.

10. The apparatus for ultrasonically characterizing a single droplet of a liquid as described in claim 7, further comprising means for sweeping the ultrasonic excitation from said means for applying ultrasonic excitation to said transducer over a chosen range of ultrasonic frequencies.

11. The apparatus for ultrasonically characterizing a single droplet of a liquid as described in claim 10, further comprising means for measuring the frequency of the standing waves generated in the droplet, whereby a resonance spectrum of the liquid droplet is obtained which is characteristic of the droplet.

12. The apparatus for ultrasonically characterizing a single droplet of a liquid as described in claim 7, further comprising means for changing the distance between the open surface of said transducer and the planar surface of said reflector.

13. The apparatus for ultrasonically characterizing a single droplet of a liquid as described in claim 7, wherein said reflector is transparent so that the droplet may be optically observed.

14. A method for ultrasonically characterizing a single droplet of a liquid, which comprises the steps of:

a. applying ultrasonic excitation having a chosen frequency to the droplet using a pair of transducers spaced a chosen distance apart where the droplet is suspended in between the tranducers by surface tension only, whereby standing waves are generated; in the droplet; and b. detecting the generated standing waves from which waves, the droplet is characterized.

15. The method for ultrasonically characterizing a single droplet of a liquid, as described in claim 14, further comprising the step of sweeping the applied frequency of ultrasonic excitation over a chosen range of frequencies, whereby a resonance spectrum of the liquid droplet is obtained which is characteristic of the droplet.

* * * * *